(12) United States Patent
Chou

(10) Patent No.: US 9,320,676 B2
(45) Date of Patent: Apr. 26, 2016

(54) RESONANCE MASSAGE DEVICE AND METHOD FOR MASSAGING THE ACUPUNCTURE POINTS ON THE WRIST

(76) Inventor: Lai Chou, Taichung (TW)

( * ) Notice: Subject to any disclaimer, the term of this patent is extended or adjusted under 35 U.S.C. 154(b) by 750 days.

(21) Appl. No.: 13/525,417

(22) Filed: Jun. 18, 2012

(65) Prior Publication Data

US 2012/0323149 A1 Dec. 20, 2012

(30) Foreign Application Priority Data

Jun. 20, 2011 (TW) .............................. 100211109 U

(51) Int. Cl.
*A61H 1/00* (2006.01)
*A61H 23/00* (2006.01)
*A61N 5/06* (2006.01)

(52) U.S. Cl.
CPC .............. *A61H 23/00* (2013.01); *A61N 5/0619* (2013.01); *A61N 2005/066* (2013.01)

(58) Field of Classification Search
CPC ... A61H 23/00; A61H 23/02; A61H 23/0218; A61H 23/0254; A61H 23/0263; A61H 39/00; A61H 39/04; A61H 2039/005; A61N 5/0169
USPC ........................ 601/15, 18, 69–72, 74, 78–81
See application file for complete search history.

(56) References Cited

U.S. PATENT DOCUMENTS

| | | | | |
|---|---|---|---|---|
| 2,422,451 | A | * | 6/1947 | Watters ............................ 135/69 |
| 4,232,678 | A | * | 11/1980 | Skovajsa ........................... 607/89 |
| 4,716,898 | A | * | 1/1988 | Chauve et al. ................ 606/204 |
| 4,981,146 | A | * | 1/1991 | Bertolucci ....................... 607/72 |
| 5,575,761 | A | * | 11/1996 | Hajianpour ...................... 601/48 |
| 2004/0167588 | A1 | * | 8/2004 | Bertolucci ....................... 607/72 |
| 2009/0177129 | A1 | * | 7/2009 | Chan et al. .................... 601/112 |
| 2010/0228304 | A1 | * | 9/2010 | Kriksunov et al. ............... 607/3 |
| 2010/0249677 | A1 | * | 9/2010 | DiUbaldi et al. ............... 601/46 |

\* cited by examiner

*Primary Examiner* — Justine Yu
*Assistant Examiner* — Kathrynn Lyddane
(74) *Attorney, Agent, or Firm* — Banger Shia

(57) ABSTRACT

A resonance massage method and device for massaging acupuncture points on the wrist, wherein the massage device is provided with two wave generators which are placed on the inner and outer wrist to output periodic waves in opposite directions, and the opposite periodic waves resonate to create resonance which is capable of persistently massaging the acupuncture points on the wrist.

9 Claims, 11 Drawing Sheets

RESONANCE MASSAGE DEVICE AND METHOD FOR MASSAGING THE ACUPUNCTURE POINTS ON THE WRIST

BACKGROUND OF THE INVENTION

1. Field of the Invention

The present invention relates to an electric massage device, and more particularly to an electric massage device which has two wave generators mounted at opposite sides of the wrist of a user to simultaneously massage the acupuncture points on the wrist by resonance.

2. Description of the Prior Art

The probability of people suffering from cardiovascular disease, digestive disease and sleep disorder is getting high due to the lifestyle of today's people changes, and accordingly, people are more concerned about the prevention of such diseases. Many Chinese medical documents have shown that stimulation to the acupuncture points indeed can prevent diseases, improve health and relieve pressure. Therefore, the non-invasive and simple acupuncture points massage has become one of the common treatment and healthcare methods.

It is to be noted that Chinese medical studies show that, as shown in FIG. 1A, there is a Neiguan acupuncture point 51 on the inner wrist 50, which is located 4-8 cm away from the lower horizontal line of the palm. Massaging the Neiguan acupuncture point 51 frequently can prevent Cardiovascular, cerebrovascular and digestive diseases. As shown in FIG. 1B, at a position on the outer wrist opposite the Neiguan acupuncture point 51, there is a Waiguan acupuncture point 52. Massaging the Waiguan acupuncture point 52 frequently can pass through the Yuanqi and improve fluid circulation, restoring menstrual flow, activating the collaterals, regulating the flow of Qi and relieving pain. The effect will be even better if the Neiguan acupuncture point 51 and the Waiguan acupuncture point 52 are massaged simultaneously.

The massage force can be easily controlled by feel to achieve a deeper massager when using finger or manual massage to massage the acupuncture points. However, manual massage can't last for a long time, and therefore, the massage effect won't be good. Hence, many vibrating electric massage device or some special metal rings with far infrared radiation, which are capable of performing massage persistently, appeared on the market.

However, the massage carried out by these electric massage devices is mostly in the form of single-point vibration. Therefore, the existing electric massage devices are unable to massage the Neiguan and Waiguan acupuncture points 51, 52 simultaneously. Furthermore, the strength of the unidirectional vibration caused by the electric massage devices has been reduced when the electric massage devices contact the skin, therefore, the stimulation to the acupuncture points is very limited. As for the special metal rings, it seems like that the special metal rings can radiate far infrared rays to the Neiguan and Waiguan acupuncture points 51, 52 simultaneously and persistently, however, the energy of the far infrared radiation is very limited.

The present invention has arisen to mitigate and/or obviate the afore-described disadvantages.

SUMMARY OF THE INVENTION

The primary object of the present invention is to provide a resonance massage method and device for massaging acupuncture points on the wrist, wherein the massage device has two wave generators placed on the wrist to output periodic waves in opposite directions, and the opposite periodic waves resonate to create resonance which is capable of persistently massaging the acupuncture points on the wrist.

To achieve the above object, a resonance massage device for massaging acupuncture points on a wrist of a user in accordance with the present invention comprises: a fixing member, two wave generators, a battery unit and a control unit. The fixing member is a hollow annular structure having two free ends engaged with each other. The fixing member is formed between the two free ends thereof with a space and further includes an inner annular surface and an outer annular surface connected to the two free ends. The inner annular surface is defines an inserting hole for insertion of the wrist and is formed with two opposite protrusions around the inserting hole, and the two protrusions are located 4-8 cm away from the wrist and placed against the wrist. The two wave generators each have a circuit board and a wave source unit disposed on the circuit board, and are disposed in the space of the fixing member and located corresponding to the protrusions. The battery unit is disposed on the fixing member and electrically connected to the circuit boards of the wave generators. The control unit is disposed in the fixing member electrically connected to the battery unit to control the wave generators to emit 60 to $7.9 \times 10^{14}$ Hz periodic waves toward the protrusions of the fixing member, and then the periodic waves are transmitted to the wrist via the protrusions to generate resonance massage.

A resonance massage method used in combination with the resonance massage device of the present invention, comprises the following steps:

inserting the wrist of the user into the inserting hole of the resonance massage device, and making the two protrusions on the inner annular surface press against a Neiguan acupuncture point which is located on an inner wrist and a Waiguan acupuncture point which is located on an outer wrist;

using the control unit to control the wave source units of the wave generators and making the wave source units emit a periodic wave with a frequency of 60 to $7.9 \times 10^{14}$ Hz or a periodic wave with a wavelength of 380 to $2.5 \times 10^4$ nm toward the protrusions, and then the periodic waves are transmitted to the Neiguan and Waiguan acupuncture points through the two protrusions;

defining that one of the periodic waves is a first periodic wave which is transmitted from the Waiguan acupuncture point to the Neiguan acupuncture point, and another one of the periodic waves is a second periodic wave which is transmitted from the Neiguan acupuncture point to the Waiguan acupuncture point, the first and second periodic waves are simultaneously transmitted between the Neiguan acupuncture point and the Waiguan acupuncture point and resonate to form a third periodic wave which has a frequency higher than that of the first and second periodic waves.

DETAILED DESCRIPTION OF THE PREFERRED EMBODIMENTS

Figure 1A:
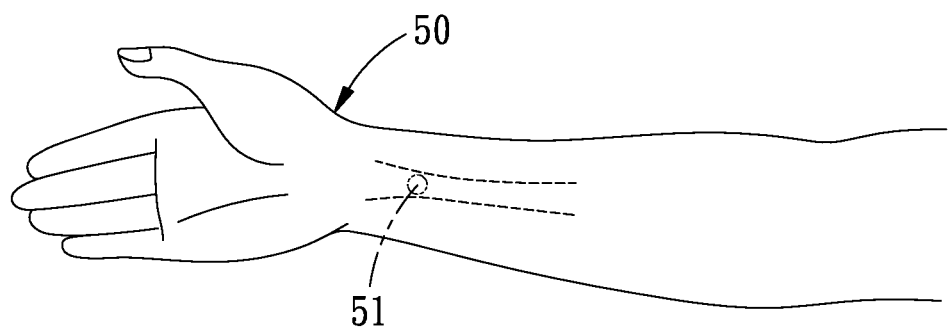
FIG. 1A shows the Neiguan acupuncture point on the wrist.

The present invention will be clearer from the following description when viewed together with the accompanying drawings, which show, for purpose of illustrations only, the preferred embodiment in accordance with the present invention.

Referring to FIGS. 2-5, a resonance massage device for massaging acupuncture points on the wrist in accordance with a preferred embodiment of the present invention is to be worn on the wrist 50 of a user and comprises: a fixing member 10, two wave generators 20, a battery unit 30 and a control unit 40.

Figure 2:
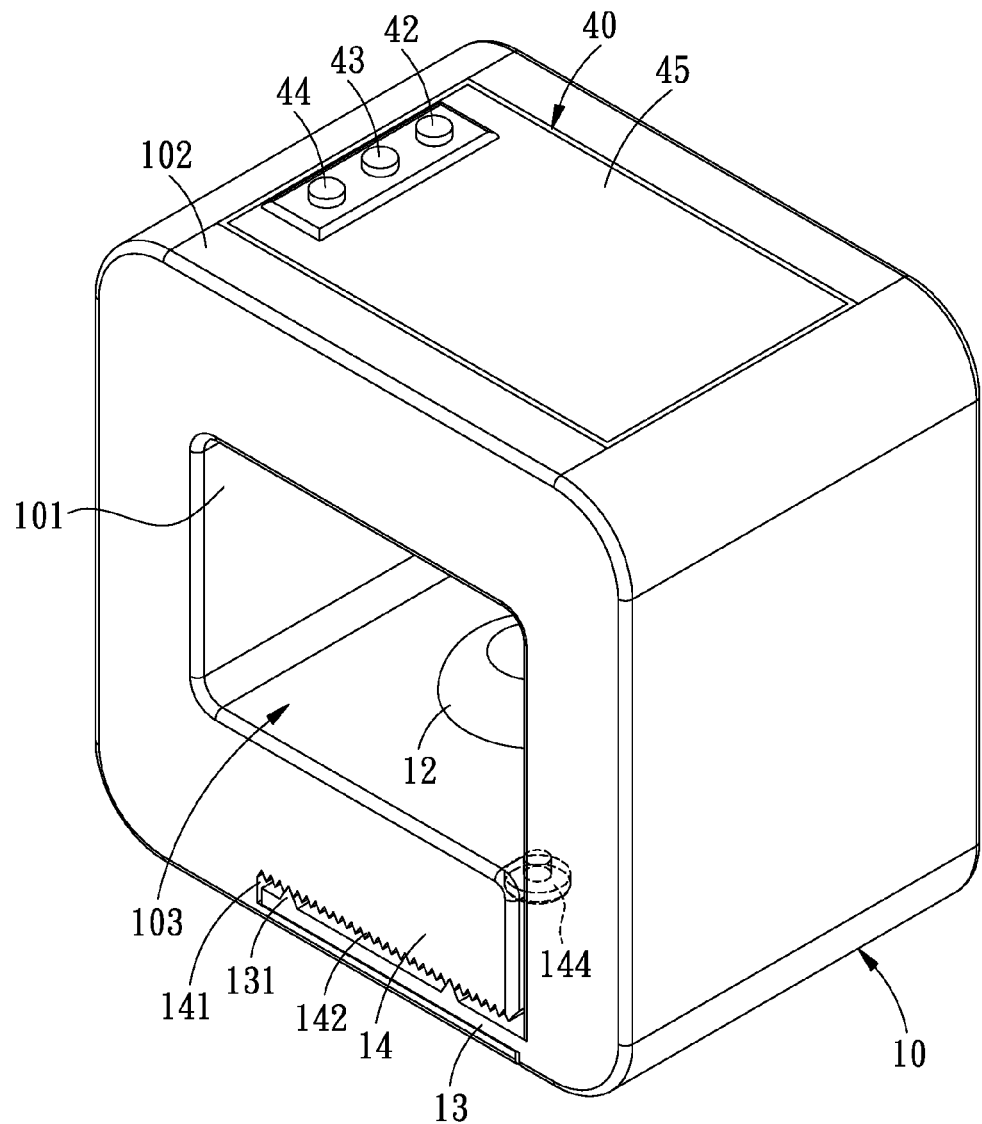
FIG. 2 is a perspective view of a resonance massage device for massaging acupuncture points on the wrist in accordance with a preferred embodiment of the present invention.
Figure 3:
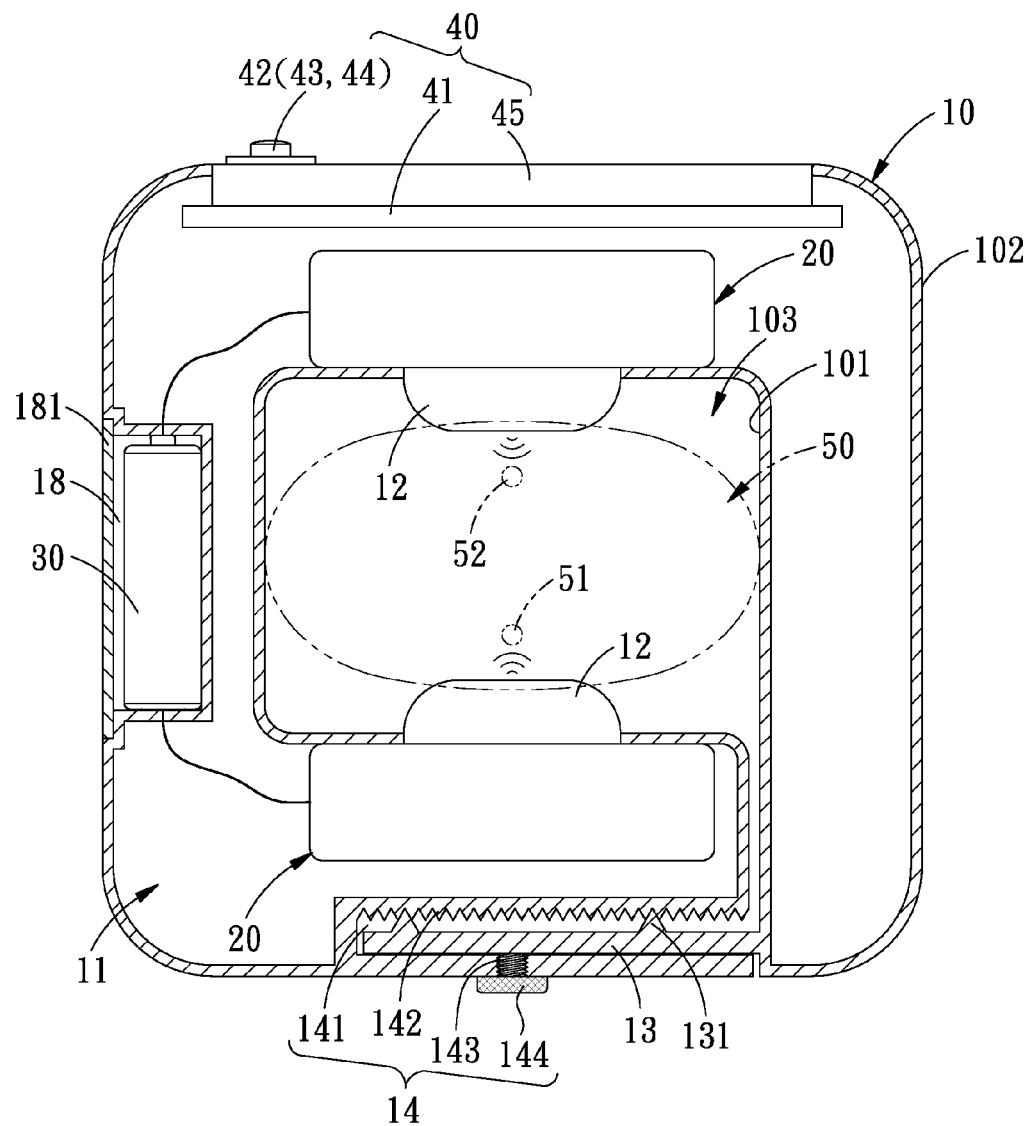
FIG. 3 is a cross sectional view of the resonance massage device for massaging acupuncture points on the wrist in accordance with the preferred embodiment of the present invention.
Figure 5:
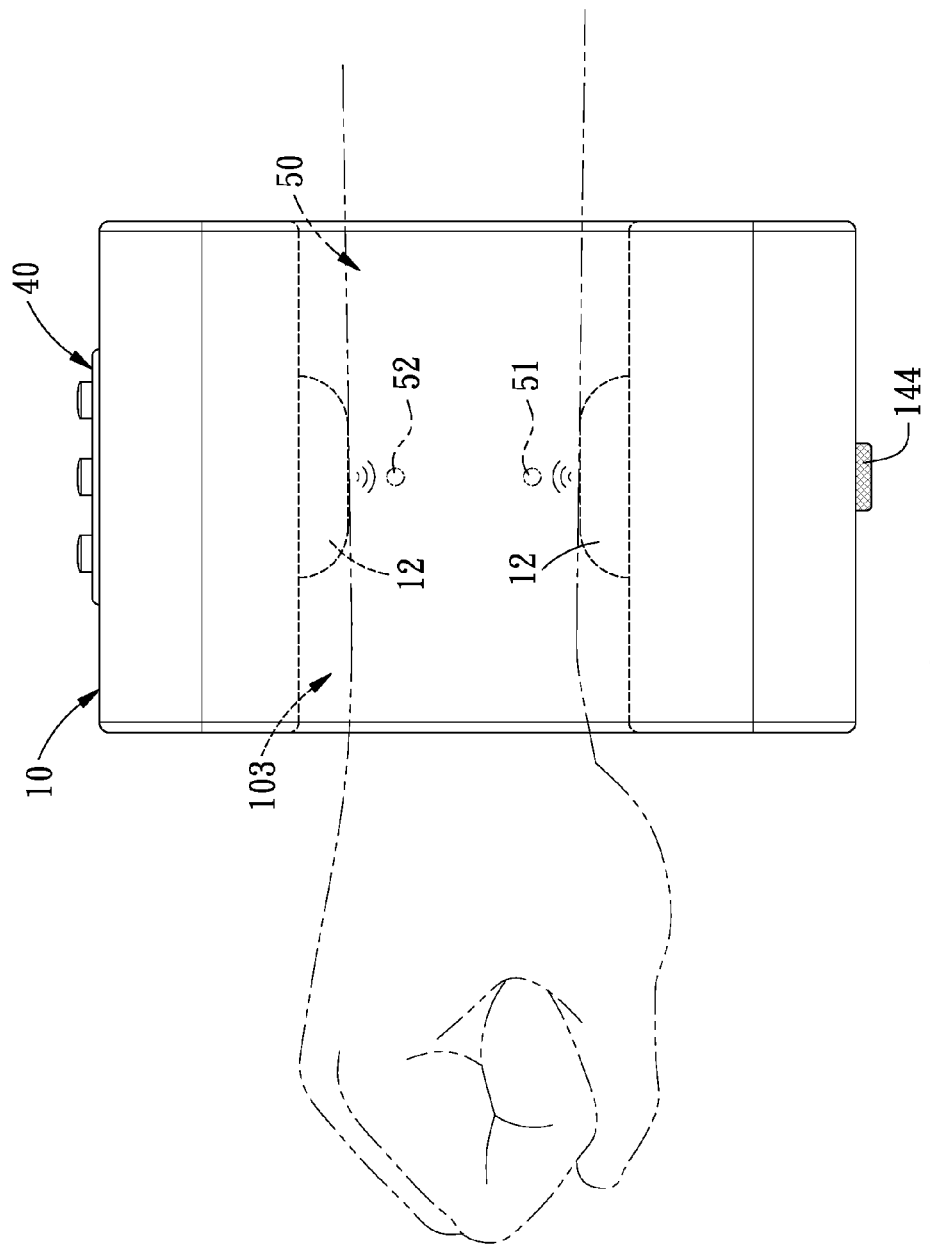
FIG. 5 shows that the resonance massage device for massaging acupuncture points on the wrist of the present invention is worn on a user's wrist.

The fixing member 10, as shown in FIGS. 2 and 3, is a hollow annular structure that has two free ends engaged with each other. The fixing member 10 is formed between the two free ends thereof with a space 11 and further includes an inner annular surface 101 and an outer annular surface 102 connected to the two free ends. The inner annular surface 101 defines an inserting hole 103 for insertion of the wrist 50 and two opposite protrusions 12 around the inserting hole 103, as shown in FIGS. 3 and 5, and the two protrusions 12 are located 4-8 cm away from the wrist 50 and placed against the inner and outer wrist.

In this embodiment, the fixing member 10 is an integrally formed flexible hollow annular structure, and the two free ends of the fixing member 10 are an engaging portion 13 and a locking portion 14. The locking portion 14 is formed with a receiving chamber 141 which is formed on an inner surface thereof adjacent to the inner annular surface 101 with a toothed surface 142. The locking portion 14 is further formed with a threaded hole 143 which is located at the outer annular surface 102 and in communication with the receiving chamber 141. The engaging portion 13 is received in the receiving chamber 141 and formed with a plurality of teeth 131 for engaging with the toothed surface 142. A bolt 144 is screwed in the threaded hole 143 to press against the engaging portion 13. By such arrangements, the size of the inserting hole 103 can be easily adjustable to fit wrists A of different sizes by changing the position of the engaging portion 13 with respect to the locking portion 14. The bolt 144 presses against the engaging portion 13 to push the protrusions 12 of the fixing member 10 against the wrist of the user, so that periodic wave can be surely transmitted into the user's body.

Referring to FIGS. 2 and 3, the two wave generators 20 each include a circuit board 21 and a wave source unit 22 disposed on the circuit board 21. The wave generators 20 are disposed in the space 11 of the fixing member 10 and located corresponding to the protrusions 12. In this embodiment, the wave generators 20 emit $60-7.9\times10^{14}$ Hz periodic waves toward the protrusions 12 of the fixing members 10, and the periodic waves are conducted in opposite directions to create resonance in the wrist 50, and consequently resulting in a resonance massage effect on the Neiguan acupuncture point 51 and the Waiguan acupuncture point 52.

Figure 4:
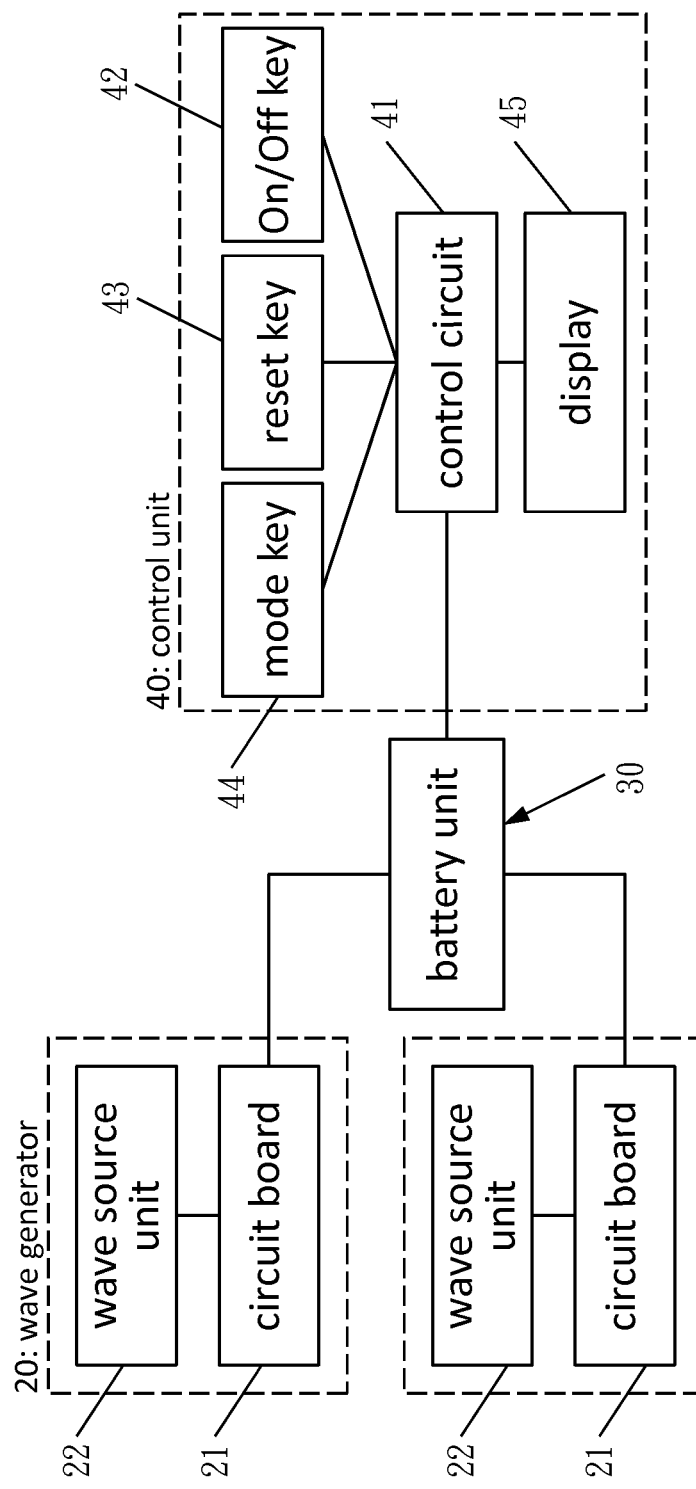
FIG. 4 is a block diagram showing the resonance massage device for massaging acupuncture points on the wrist in accordance with the preferred embodiment of the present invention.

Referring to FIGS. 3 and 4, the outer annular surface 102 of the fixing member 10 is formed with a receiving groove 18 for holding the battery unit 30, the receiving groove 18 is sealed with a cover 181, and the battery unit 30 is electrically connected to the circuit boards 21 of the two wave generators 20. The control unit 40 is electrically connected to the battery unit 30 to control the wave generators 20 to emit periodic waves toward the protrusions 12 of the fixing member 10, and then the periodic waves are transmitted to the wrist via the protrusions 12 to generate resonance massage. In this embodiment, the control unit 40 includes a control circuit 41 electrically connected to the battery unit 30, a display 45 embedded in the outer annular surface 102 of the fixing member 10 and electrically connected to the control circuit 41, and an On/Off key 42, a reset key 43 and mode key 44 which are electrically connected to the control circuit 41.

The periodic wave generated by the wave source units 22 of the wave generators 20 can be selected from the group consisting of shock wave, sonic wave, ultrasonic wave, electromagnetic wave, far infrared wave, light wave, and biological massage wave. The frequency from the shock wave is preferably $3.6\times10^3$ to $40\times10^3$ Hz, the sonic wave is preferably 20 to $20\times10^3$ Hz, the ultrasonic wave is preferably $20\times10^3$ to $20\times10^6$ Hz, and the electromagnetic wave is preferably 20 to $20\times10^3$ Hz. The wavelength of the far infrared wave is preferably $3\times10^3$ to $2.5\times10^4$ nm, and that of the light wave is preferably 380-780 nm.

Figure 6:
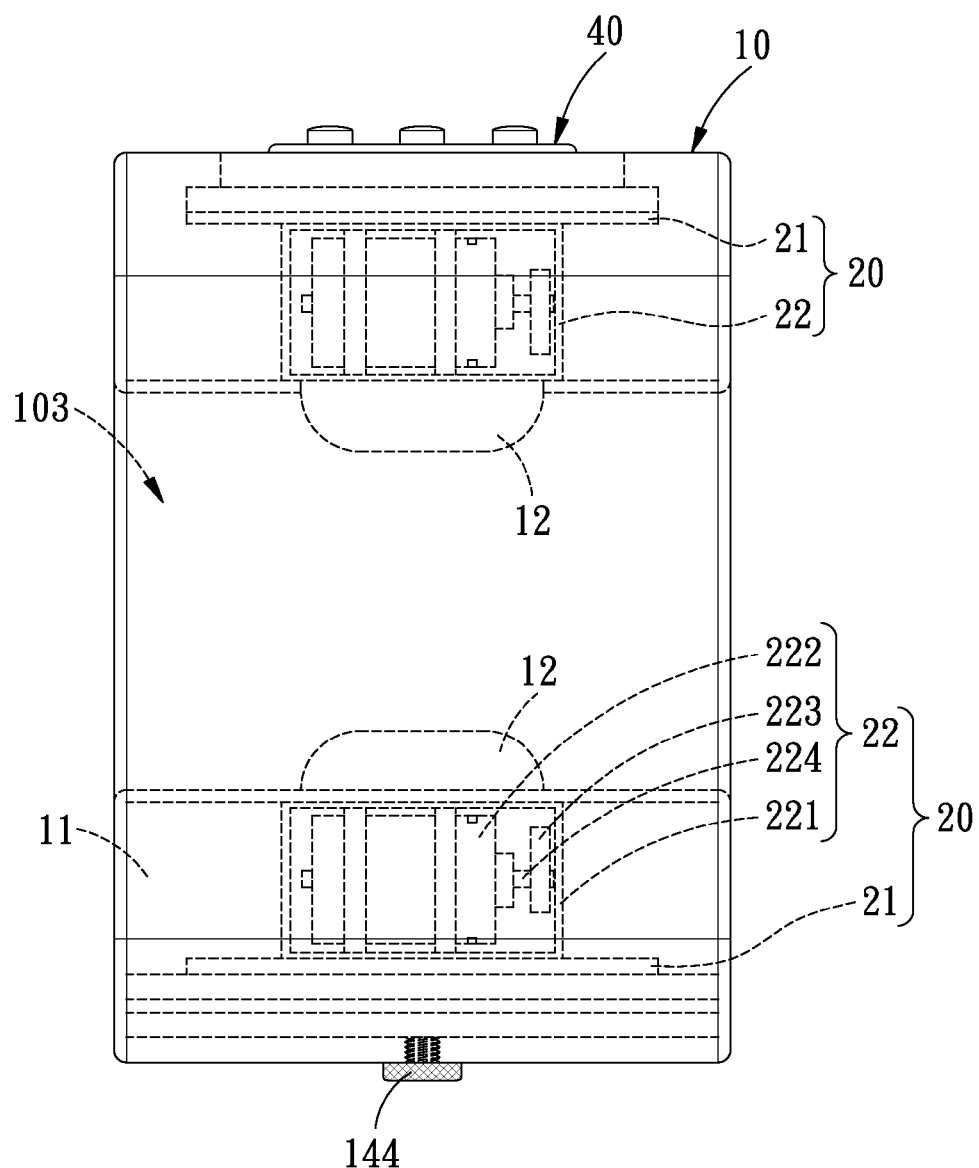
FIG. 6 is a perspective view of a resonance massage device for massaging acupuncture points on the wrist in accordance with the present invention, wherein the wave generators are vibration motors.
Figure 7:
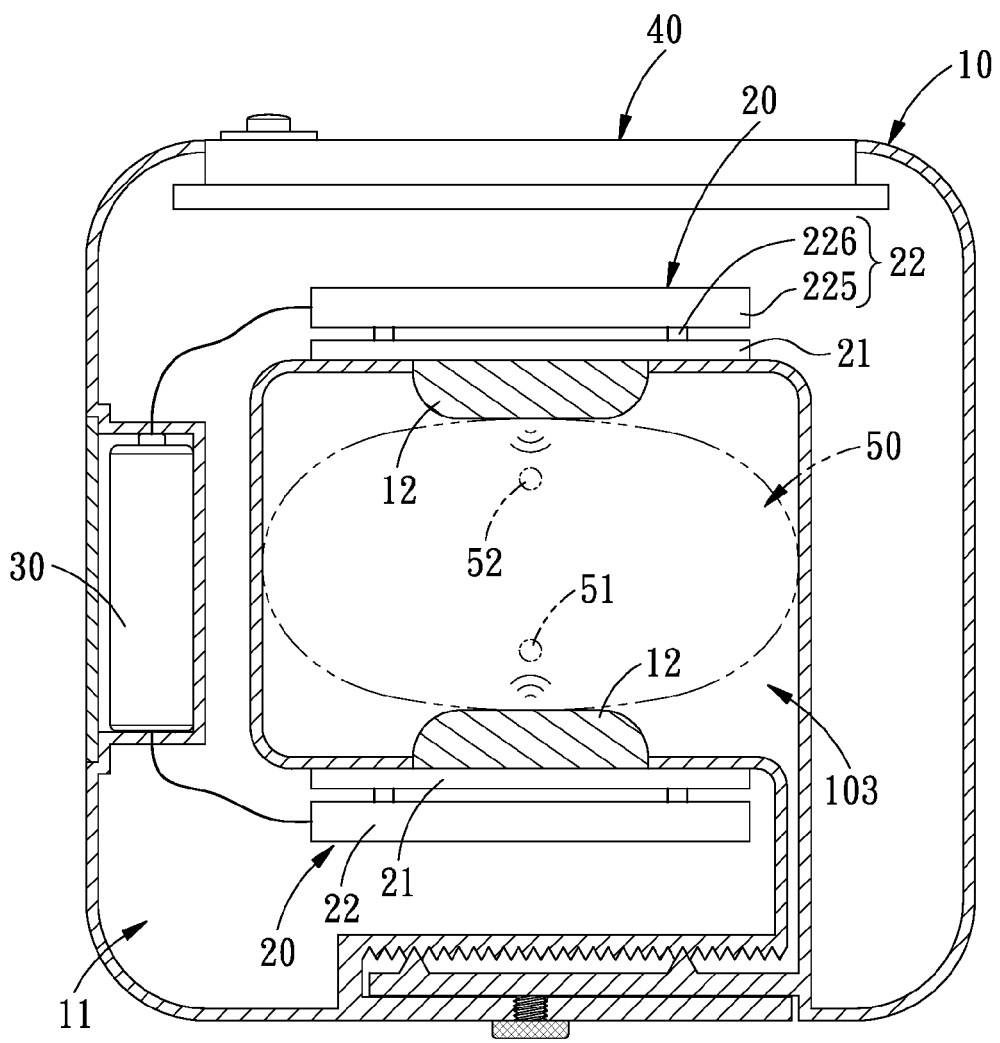
FIG. 7 is a perspective view of a resonance massage device for massaging acupuncture points on the wrist in accordance with the present invention, wherein the wave generators are crystal oscillators.

As shown in FIG. 6, when emitting shock waves, the wave source units 22 can be a vibration motor. The protrusions 12 of the fixing member 10 are in the form of solid massage blocks. The wave source units 22 each include a housing 221 and a power source 222 disposed in the housing 221. The power source 222 has a drive shaft 223 which is used to rotate an eccentric block 224 disposed at the end of the drive shaft 223, so as to generate shock wave. As shown in FIG. 7, the wave source unit 22 is a crystal oscillator which includes a base 225 formed with a plurality of terminals 226 to be engaged on the circuit boards 21, when the base 225 is powered on, it will produce shock waves.

Figure 8:
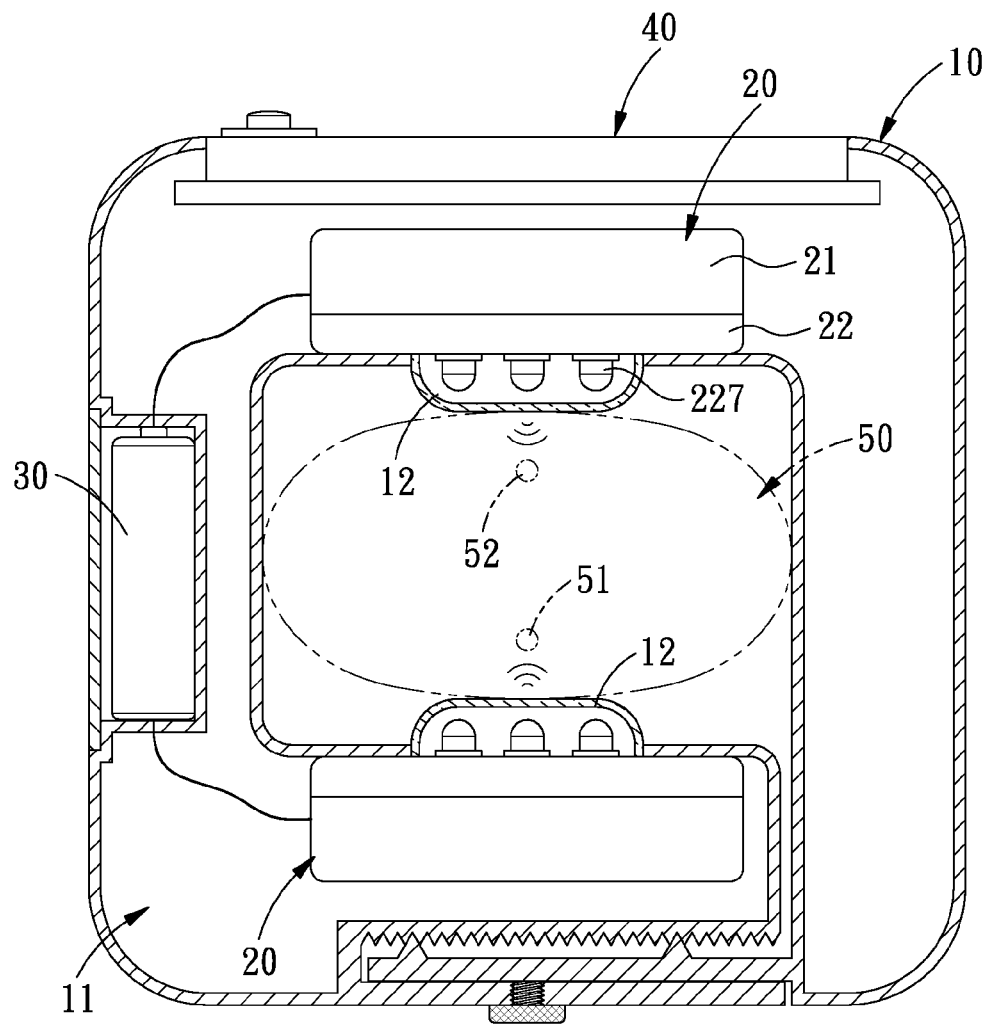
FIG. 8 is a perspective view of a resonance massage device for massaging acupuncture points on the wrist in accordance with the present invention, wherein the wave generators are electromagnetic wave generators.

As shown in FIG. 8, the protrusions 12 of the fixing member 10 are hollow covers. The wave source unit 22 is an electromagnetic wave generator provided with a far infrared ray generator 227, and the far infrared ray generator 227 is disposed inside the protrusions 12 and emits far infrared ray toward the acupuncture points on the wrist 50.

Figure 9:
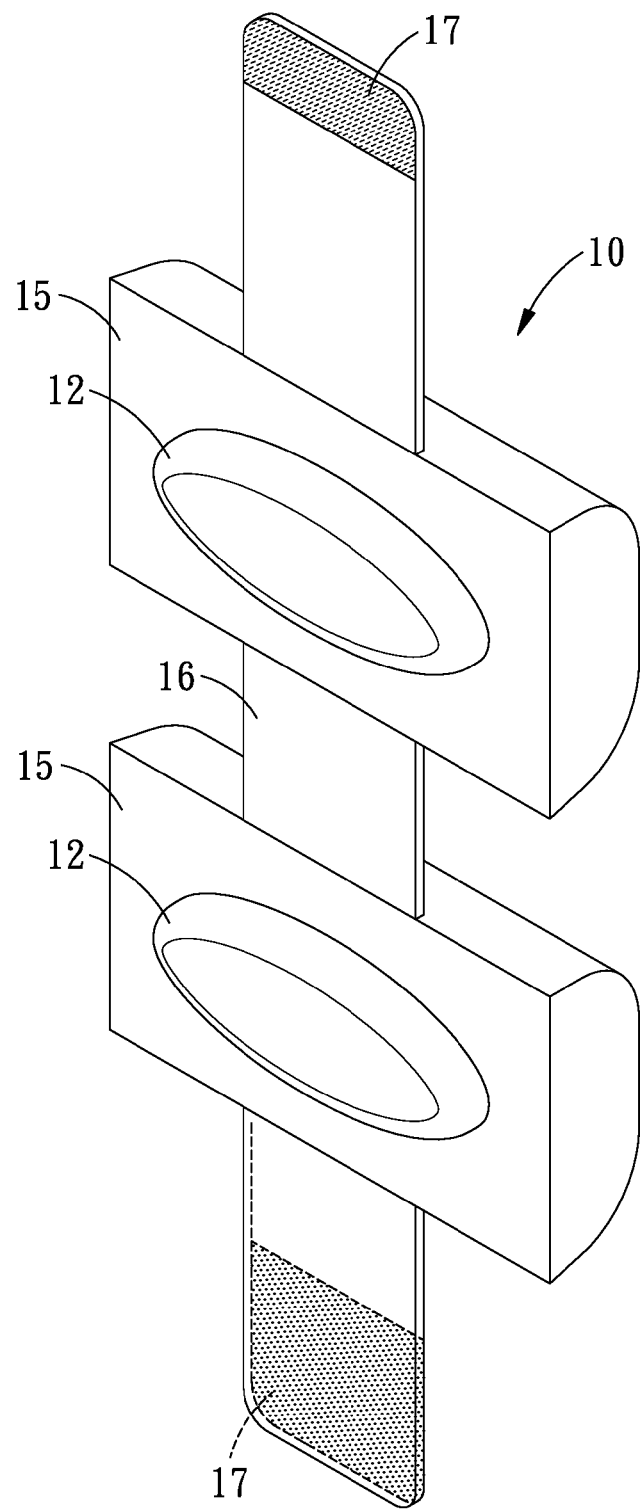
FIG. 9 is a perspective view of a resonance massage device for massaging acupuncture points on the wrist in accordance with another embodiment of the present invention.
Figure 10:
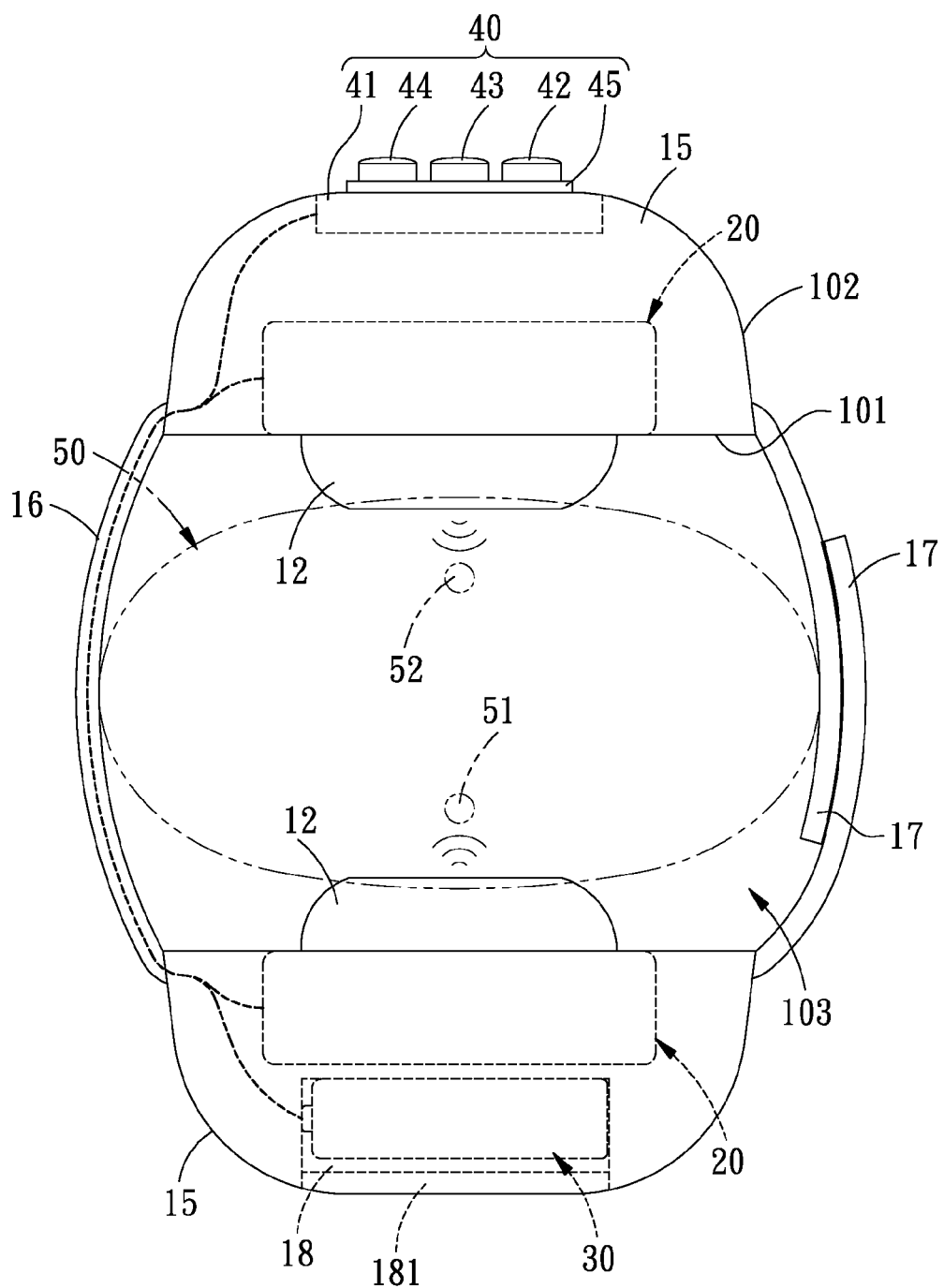
FIG. 10 is a perspective view of a resonance massage device for massaging acupuncture points on the wrist in accordance with another embodiment of the present invention.
Figure 11:
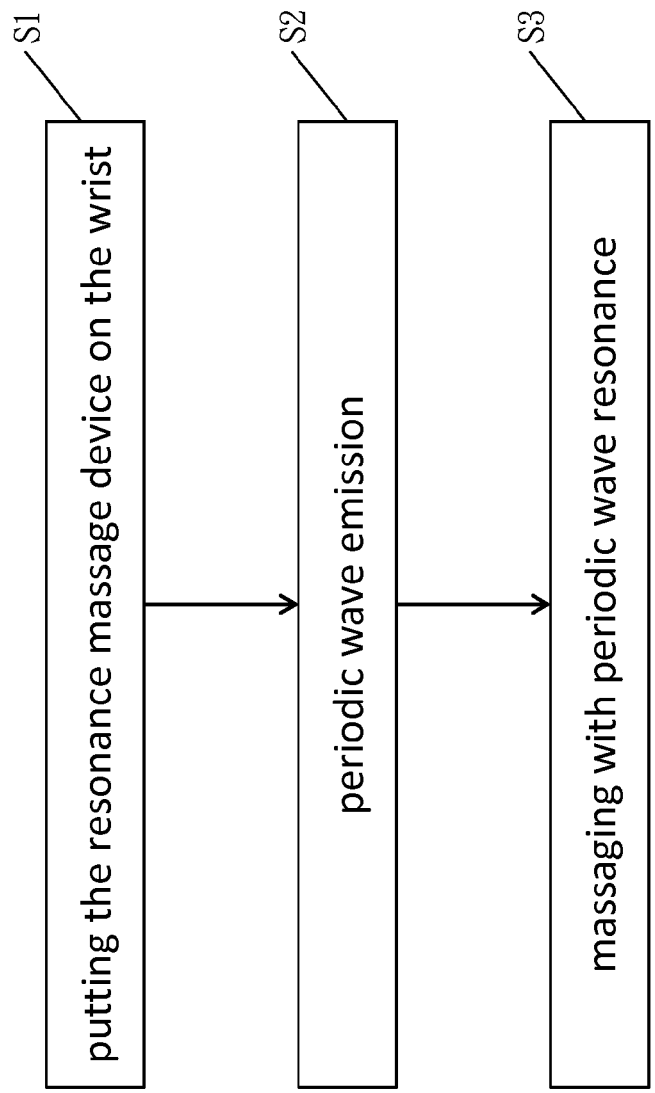
FIG. 11 is a flow chart showing the steps of the massage method used in combination with the resonance massage device for massaging acupuncture points on the wrist in accordance with the present invention.

Referring then to FIGS. 4, 9 and 10, a resonance massage device for massaging acupuncture points on the wrist in accordance with another preferred embodiment of the present invention is provided with two receiving portions 15 at the middle of the fixing member 10, and the two receiving portions 15 are connected by a connecting portion 16. The receiving portions 15 each are a hollow structure with one side connected to the connecting portion 16 and another side connected to a free end of the fixing member 10. The free ends of the fixing member 10 each are formed with a hook-and-loop tape 17. The connecting portion 16 is a hollow elastic member and in communication with the interior of the two receiving portions 15 constitute the space 11 inside the fixing member 10. Then, the two free ends of the fixing member 10 are fastened together by the hook-and-loop tapes 17 to make the fixing member 10 become an annular structure with the inner and outer annular surface 101, 102. The protrusions 12 are formed on the receiving portions 15 and located around the inner annular surface 101. In each of the receiving portions 15 is formed a wave generator 20, and the battery unit 30 is disposed in one of the receiving portions 15. The two wave generators 20, the battery unit 30 and the control unit 40 are electrically connected by the connecting portion 16.

Referring then to FIGS. 3, 5, 7 and 11, there is a Neiguan acupuncture point 51 on the inner wrist 50, and at a position on the outer wrist opposite the Neiguan acupuncture point 51, there is a Waiguan acupuncture point 52. A resonance massage method used in combination with the resonance massage device for massaging acupuncture points on the wrist in accordance with the preferred embodiment of the present invention comprises the following steps:

S1 putting the resonance massage device on the wrist: inserting the wrist of a user into the inserting hole 103 of the resonance massage device, and making the two protrusions 12 on the inner annular surface 101 press against the Neiguan acupuncture point 51 and the Waiguan acupuncture point 52.

S2 periodic wave emission: using the control unit 40 to control the wave source units 22 of the wave generators 20 and making the wave source units 22 emit a periodic wave with a frequency of 20 to $20 \times 10^6$ Hz or a periodic wave with a wavelength of 380 to $2.5 \times 10^4$ nm toward the protrusions 12, and then the periodic waves are transmitted to the Neiguan and Waiguan acupuncture points 51, 52 through the two protrusions 12.

S3 massaging with periodic wave resonance: defining that one of the periodic waves is a first periodic wave which is transmitted from the Waiguan acupuncture point 52 to the Neiguan acupuncture point 51, and the other one of the periodic waves is a second periodic wave which is transmitted from the Neiguan acupuncture point 51 to the Waiguan acupuncture point 52. The first and second periodic waves are simultaneously transmitted between the Neiguan acupuncture point 51 and the Waiguan acupuncture point 52 and resonate to form a third periodic wave which has a frequency higher than that of the first and second periodic waves.

In this embodiment, the first and second periodic waves have the same frequency and massage the Neiguan and Waiguan acupuncture points 51, simultaneously by resonance, and the frequency is preferably $1 \times 10^4 \pm 3.5 \times 10^3$ Hz. The first and second periodic waves can also have different frequencies.

The attachments show the results of the bio-impedance value test conducted on two testees by using Ryodoraku, wherein the data shown in the top half of the respective attachments are the bio-impedance values of the specific organs obtained by testing the left and right halves of the body of the testees. The lower half of the respective attachments shows a comparison between the bio-impedance values of the specific organs of the testees and a personalized average bio-impedance value, wherein the average bio-impedance value is calculated based on the abovementioned bio-impedance values, and the bio-impedance values of the specific organs of the testees are connected to form the curves. The smaller the amplitude of the curves, the better.

The First Testee

Figure 1B:
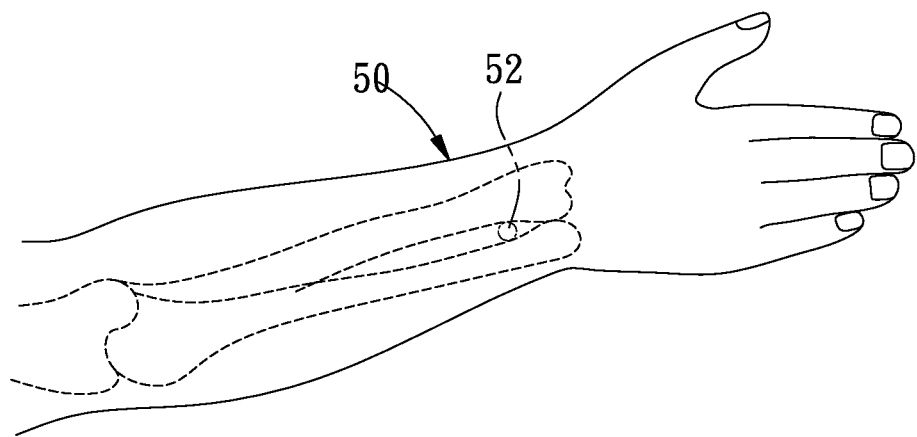
FIG. 1B shows the Waiguan acupuncture point on the wrist.

As shown in the attachment 1-1, before the first testee is massaged with the resonance massage device of the present invention, the average bio-impedance value of the first testee is 103, and the amplitude of the curve at the positions corresponding to the spleen, bladder, gallbladder is big, and the maximum deviation of the curve (at these three positions) from the average value is over 30. The attachment 1-2 shows that, after massaging the acupuncture points on the wrist of the first testee by using the resonance massage device of the present invention for 20 minutes, the maximum deviation of the curve (at these three positions) from the average bio-impedance value is decreased to below 20, and then, as shown in FIG. 1-3, the amplitude of the curve becomes smaller after the acupuncture points on the wrist of the first testee are massaged by the resonance massage device of the present invention for 60 minutes.

The Second Testee

As shown in the attachment 2-1-1 and 2-1-2, before the second testee is massaged with the resonance massage device of the present invention, the average bio-impedance value of the first testee is 77, and the amplitude of the curve at the positions corresponding to the small intestine, liver, kidney, and gallbladder is big, and the maximum deviation of the curve (at these four positions) from the average value is over 30. The attachment 2-2 shows that, after massaging the acupuncture points on the wrist of the second testee by using the resonance massage device of the present invention for 40 minutes, the maximum deviation of the curve from the average bio-impedance value is decreased to below 20, and then the amplitude of the curve becomes smaller.

Hence, the bio-impedance value test conducted on two testees shows that the periodic-wave caused resonance massage on the acupuncture points of the wrist performed by the massage device of the present invention can relieve pain and other symptoms, accelerating blood circulation and removal of impurities from the body. Furthermore, the massage method and device of the present invention provide a better effect of health improvement than the conventional method of massaging by inputting periodic wave in a unidirectional way.

While we have shown and described various embodiments in accordance with the present invention, it is clear to those skilled in the art that further embodiments may be made without departing from the scope of the present invention.

What is claimed is:

1. A resonance massage device for massaging acupuncture points on a wrist of a user, to be worn on the wrist of the user, comprising:

a fixing member having two free ends engaged with each other to define a space and further including an inner annular surface and an outer annular surface connected to the two free ends, the inner annular surface defining an inserting hole for insertion of the wrist and being formed with two opposite protrusions which are adapted to massage the wrist;

two wave generators each having a circuit board and a wave source unit disposed on the circuit board and being disposed in the space of the fixing member and located corresponding to the protrusions;

a battery unit disposed on the fixing member and electrically connected to the circuit boards of the wave generators; and a control unit disposed in the fixing member electrically connected to the battery unit to control the wave generators to emit periodic waves toward the protrusions of the fixing member to generate resonance massage;

wherein the fixing member is a flexible hollow annular structure, the two free ends of the fixing member are an engaging portion and a locking portion, the locking portion is formed with a receiving chamber which is formed on an inner surface thereof adjacent to the inner annular surface with a toothed surface, the locking portion is further formed with a threaded hole which is located at the outer annular surface and in communication with the receiving chamber, the engaging portion is received in the receiving chamber and formed with a plurality of teeth for engaging with the toothed surface, and a bolt is screwed in the threaded hole to press against the engaging portion;

wherein at least one of the protrusions of the fixing member is in the form of a solid massage block, and at least one of the wave source units is a vibration motor for outputting $3.6 \times 10^3$ to $40 \times 10^3$ Hz periodic waves to the solid massage block.

2. The resonance massage device as claimed in claim 1, wherein the outer annular surface of the fixing member is formed with a receiving groove for holding the battery unit, and the receiving groove is sealed with a cover.

3. The resonance massage device as claimed in claim 1, wherein the control unit includes a control circuit electrically connected to the battery unit, a display embedded in the outer annular surface of the fixing member and electrically connected to the control circuit, and an on/off key, a reset key and mode key which are electrically connected to the control circuit.

4. A resonance massage device for massaging acupuncture points on a wrist of a user, to be worn on the wrist of the user, comprising:

a fixing member having two free ends engaged with each other to define a space and further including an inner annular surface and an outer annular surface connected to the two free ends, the inner annular surface defining an inserting hole for insertion of the wrist and being formed with two opposite protrusions which are adapted to massage the wrist;

two wave generators each having a circuit board and a wave source unit disposed on the circuit board and being disposed in the space of the fixing member and located corresponding to the protrusions;

a battery unit disposed on the fixing member and electrically connected to the circuit boards of the wave generators; and a control unit disposed in the fixing member electrically connected to the battery unit to control the wave generators to emit periodic waves toward the protrusions of the fixing member to generate resonance massage; wherein two receiving portions are provided at a middle of the fixing member, and the two receiving portions are connected by a connecting portion, the receiving portions each are a hollow structure with one side connected to the connecting portion and another side connected to one of the free ends of the fixing member, the free ends of the fixing member each are formed with a hook-and-loop tape, the connecting portion is a hollow elastic member and in communication with an interior of the two receiving portions to constitute the space of the fixing member, the two free ends of the fixing member are fastened together by the hook-and-loop tapes to make the fixing member become an annular structure with the inner and outer annular surface, the protrusions are formed on the receiving portions and located around the inner surface, in each of the receiving portions is formed one of the wave generators, and the battery unit is disposed in one of the receiving portions, and the two wave generators, the battery unit and the control unit are electrically connected by the connecting portion;

wherein at least one of the protrusions of the fixing member is in the form of a solid massage block, and at least one of the wave source units is a vibration motor for outputting $3.6 \times 10^3$ to $40 \times 10^3$ Hz periodic waves to the solid massage block.

5. A resonance massage device for massaging acupuncture points on a wrist of a user, to be worn on the wrist of the user, comprising:

a fixing member having two free ends engaged with each other to define a space and further including an inner annular surface and an outer annular surface connected to the two free ends, the inner annular surface defining an inserting hole for insertion of the wrist and being formed with two opposite protrusions which are adapted to massage the wrist;

two wave generators each having a circuit board and a wave source unit disposed on the circuit board and being disposed in the space of the fixing member and located corresponding to the protrusions;

a battery unit disposed on the fixing member and electrically connected to the circuit boards of the wave generators; and a control unit disposed in the fixing member electrically connected to the battery unit to control the wave generators to emit periodic waves toward the protrusions of the fixing member to generate resonance massage;

wherein the fixing member is a flexible hollow annular structure, the two free ends of the fixing member are an engaging portion and a locking portion, the locking portion is formed with a receiving chamber which is formed on an inner surface thereof adjacent to the inner annular surface with a toothed surface, the locking portion is further formed with a threaded hole which is located at the outer annular surface and in communication with the receiving chamber, the engaging portion is received in the receiving chamber and formed with a plurality of teeth for engaging with the toothed surface, and a bolt is screwed in the threaded hole to press against the engaging portion;

wherein at least one of the protrusions of the fixing member is in the form of a solid massage block, and at least one of the wave source units is a crystal oscillator for outputting $3.6 \times 10^3$ to $40 \times 10^3$ Hz periodic waves to the solid massage block.

6. A resonance massage device for massaging acupuncture points on a wrist of a user, to be worn on the wrist of the user, comprising:

a fixing member having two free ends engaged with each other to define a space and further including an inner annular surface and an outer annular surface connected to the two free ends, the inner annular surface defining an inserting hole for insertion of the wrist and being formed with two opposite protrusions which are adapted to massage the wrist;

two wave generators each having a circuit board and a wave source unit disposed on the circuit board and being disposed in the space of the fixing member and located corresponding to the protrusions;

a battery unit disposed on the fixing member and electrically connected to the circuit boards of the wave generators; and a control unit disposed in the fixing member electrically connected to the battery unit to control the wave generators to emit periodic waves toward the protrusions of the fixing member to generate resonance massage;

wherein the fixing member is a flexible hollow annular structure, the two free ends of the fixing member are an engaging portion and a locking portion the locking portion is formed with a receiving chamber which is formed on an inner surface thereof adjacent to the inner annular surface with a toothed surface, the locking portion is further formed with a threaded hole which is located at the outer annular surface and in communication with the receiving chamber, the engaging portion is received in the receiving chamber and formed with a plurality of teeth for engaging with the toothed surface, and a bolt is screwed in the threaded hole to press against the engaging portion;

wherein at least one of the protrusions of the fixing member is a hollow cover, and at least one of the wave source units is an electromagnetic wave generator provided with a far infrared ray generator for outputting 380 to $2.5 \times 10^4$ nm periodic waves to the hollow cover.

7. A resonance massage method used in combination with a resonance massage device for massaging acupuncture points on the wrist of a user, comprises the following steps:

inserting the wrist of the user into an inserting hole of the resonance massage device, and making two protrusions on an inner annular surface of the resonance massage device press against a Neiguan acupuncture point which is located on an inner wrist and a Waiguan acupuncture point which is located on an outer wrist;

using a control unit to control wave source units of wave generators and making the wave source units emit a periodic wave with a frequency of 60 to $7.9 \times 10^{14}$ Hz or a periodic wave with a wavelength of 380 to $2.5 \times 10^4$ nm toward the protrusions, and then the periodic waves are transmitted to the Neiguan and Waiguan acupuncture points through the two protrusions;

defining that one of the periodic waves is a first periodic wave which is transmitted from the Waiguan acupuncture point to the Neiguan acupuncture point, and another one of the periodic waves is a second periodic wave which is transmitted from the Neiguan acupuncture point to the Waiguan acupuncture point, the first and second periodic waves are simultaneously transmitted between the Neiguan acupuncture point and the Waiguan acupuncture point and resonate to form a third periodic wave which has a frequency higher than that of the first and second periodic waves.

8. The resonance massage method as claimed in claim 7, wherein the first and second periodic waves have the same frequency which is preferably $1 \times 10^4 \pm 3.5 \times 10^3$ Hz.

9. The resonance massage method as claimed in claim 7, wherein the first and second periodic waves have different frequencies.

* * * * *